(12) United States Patent
Kawanishi et al.

(10) Patent No.: US 7,367,711 B2
(45) Date of Patent: *May 6, 2008

(54) TYPE IDENTIFICATION SYSTEM FOR DIESEL OIL AND METHOD FOR IDENTIFYING TYPE OF DIESEL OIL

(75) Inventors: Toshiaki Kawanishi, Ageo (JP); Takayuki Takahata, Ageo (JP); Kiyoshi Yamagishi, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 169 days.

This patent is subject to a terminal disclaimer.

(21) Appl. No.: 10/564,332

(22) PCT Filed: Jul. 9, 2004

(86) PCT No.: PCT/JP2004/009851

§ 371 (c)(1),
(2), (4) Date: Jan. 11, 2006

(87) PCT Pub. No.: WO2005/005970

PCT Pub. Date: Jan. 20, 2005

(65) Prior Publication Data

US 2006/0187999 A1 Aug. 24, 2006

(30) Foreign Application Priority Data

Jul. 11, 2003 (JP) ............................. 2003-195693

(51) Int. Cl.
*G01N 25/00* (2006.01)

(52) U.S. Cl. .................. 374/45; 73/61.46; 123/406.12

(58) Field of Classification Search ................. 374/45; 73/61.46; 123/406.12
See application file for complete search history.

(56) References Cited

U.S. PATENT DOCUMENTS

| | | | |
|---|---|---|---|
| 6,588,253 B2 * | 7/2003 | Lambert et al. | ........... 73/53.01 |
| 6,681,624 B2 | 1/2004 | Furuki et al. | |
| 7,152,582 B2 * | 12/2006 | Takahata et al. | ....... 123/406.12 |
| 7,168,300 B2 * | 1/2007 | Kawanishi et al. | ........ 73/61.46 |

FOREIGN PATENT DOCUMENTS

| | | |
|---|---|---|
| EP | 1 538 438 A1 | 6/2005 |
| EP | 1 548 432 A1 | 6/2005 |
| JP | 61-243352 A | 10/1986 |
| JP | 3-262949 A | 11/1991 |
| JP | 11-118566 A | 4/1999 |
| JP | 11-153561 A | 6/1999 |
| JP | 2004-101385 A | 4/2004 |
| JP | 2004-125465 A | 4/2004 |
| WO | WO 01/44761 A1 | 6/2001 |

* cited by examiner

*Primary Examiner*—Edward Lefkowitz
*Assistant Examiner*—Megann E Vaughn
(74) *Attorney, Agent, or Firm*—The Webb Law Firm, P.C.

(57) ABSTRACT

Apparatus and method for identifying type and distillation properties of light oil. A pulse voltage is applied for a predetermined period of time to a liquid type identification sensor heater comprising a heater and an identification liquid temperature sensor provided in the vicinity of the heater; the light oil to be identified is heated by the heater; and the liquid type is identified with a voltage output difference V0, corresponding to a temperature difference between the initial temperature and the peak temperature of the identification liquid temperature sensor.

21 Claims, 17 Drawing Sheets

TYPE IDENTIFICATION SYSTEM FOR DIESEL OIL AND METHOD FOR IDENTIFYING TYPE OF DIESEL OIL

BACKGROUND OF THE INVENTION

1. Field of the Invention

The present invention relates to a liquid type identification apparatus for a light oil, for identifying the type and distillation properties of a light oil, and a liquid type identification method for a light oil.

2. Background Art

Automobile exhaust gases contain contaminants such as unburned hydrocarbons (HCs), NOx gases, and SOx gases. An attempt to reduce these contaminants has hitherto been made, for example, by a method in which, for SOx, S in the light oil is removed, or unburned HCs are burned in the presence of a catalyst.

Specifically, as shown in FIG. 16, in an automobile system 100, air is introduced through an automatic element (filter) 102, is then passed through an air flow rate sensor 104, and is fed into an engine 106. On the other hand, a light oil within a light oil tank 108 is fed through a light oil pump 110 into the engine 106.

Further, the automobile system 100 is constructed so that, based on the results of detection with an A/F sensor 112, fuel injection in the engine 106 is controlled by a fuel injection control device 114 so that the air-fuel ratio is brought to a predetermined theoretical air-fuel ratio.

An exhaust gas from the engine 106 is fed into a catalyst device 116 where hydrocarbons (HCs) contained in the exhaust gas are burned. The exhaust gas is then passed through an oxygen concentration sensor 118 and is discharged as an exhaust gas.

PROBLEMS TO BE SOLVED BY THE INVENTION

In the above automobile system, as shown in FIG. 17, various light oils different from each other in distillation properties (different from each other in easiness in evaporation) are sold around the world.

Specifically, FIG. 17 shows distillation properties of light oils, that is, the relationship between % distillate and temperature. For example, 50% (T50) on the abscissa indicates the temperature (° C.) at which 50% of various light oils are evaporated.

As shown in FIG. 17, for example, as compared with a standard light oil of U.S.A., a light oil A of Honshu is the heaviest (difficult to evaporate) light oil, and a standard light oil D of Sweden is the lightest (easy to evaporate) light oil.

Accordingly, as shown in Table 1 below, for example, in an automobile regulated so that, for the standard light oil of U.S.A., the air-fuel ratio is a theoretical one, when the standard light oil of U.S.A. was replaced with the heavier light oil A of Honshu, in particular, the torque is insufficient when an engine is started, particularly when an engine in which a catalyst device is not in a warmed state is started, although the content of HCs in the exhaust gas is low.

Conversely, when the standard oil D of Sweden which is a lighter light oil is used, the air-fuel ratio exceeds the theoretical air-fuel ratio although the torque is satisfactory. In this case, in particular, when an engine is started, particularly when an engine in which a catalyst device is not in a warmed state is started, the content of HCs in the exhaust gas is so large that the influence on the environment is disadvantageously large.

TABLE 1

| Regulation light oil | Light oil used | Torque | Exhaust gas (HC) |
|---|---|---|---|
| standard light oil of U.S.A. | standard light oil C of U.S.A. | ○ | ○ |
| standard light oil of U.S.A. | light oil A of Honshu | x | ○ |
| standard light oil of U.S.A. | standard light oil D of Sweden | ○ | x |

In patent document 1, the present inventors have already proposed a fluid identification method which comprises energizing a heating element to generate heat, heating a temperature detector with this heat, giving a thermal influence on thermal transfer from the heating element to the temperature detector by the fluid to be identified, and judging the type of the fluid to be identified based on electrical output corresponding to the electrical resistance of the temperature detector. In this method, energization of the heating element is periodically carried out.

In this fluid identification method, however, since the heating element should be periodically energized (using multipulses), a lot of time is required for identification and, consequently, it is difficult to instantaneously identify the fluid. Further, in this method, for example, fluid identification can be carried out using representative values for substances considerably different from each other in properties, for example, for water, air, and oil. However, for the identification between the above light oils which have considerably mutually close properties, accurate and rapid identification are difficult.

Patent document 1: Japanese Laid-Open Patent Publication No. Hei 11 (1999)-153561 (particularly, see paragraphs [0042] to [0049])

In view of the above situation, an object of the present invention is to provide a liquid type identification apparatus for a light oil, which can identify, in an accurate and rapid manner, the type and distillation properties of light oils having various compositions different from each other in distillation properties, and to provide a liquid identification method for a light oil.

Another object of the present invention is to provide a liquid type identification apparatus for an automobile light oil using the above liquid type identification apparatus for a light oil and the liquid type identification method for a light oil, and to provide a liquid type identification method for an automobile light oil.

A further object of the present invention is to provide an automobile exhaust gas reducing apparatus, using the above liquid type identification apparatus for a light oil and the liquid type identification method for a light oil, which can efficiently reduce the exhaust gas and can improve fuel consumption, and to provide an automobile exhaust gas reducing method.

SUMMARY OF THE INVENTION

The present invention has been made with a view to solving the above problems of the prior art and to attaining the above objects. According to the present invention, there is provided a liquid type identification apparatus for a light oil, for identifying the type and distillation properties of a light oil, comprising:

a liquid type identification chamber for a light oil, for allowing a light oil to be identified, which has been introduced into a liquid type identification apparatus body, to temporarily stay therein;

a liquid type identification sensor heater provided within the light oil type identification chamber; and a liquid temperature sensor spaced by a given distance from the liquid type identification sensor heater and provided within the light oil type identification chamber, the liquid type identification sensor heater comprising a heater and an identification liquid temperature sensor provided in the vicinity of the heater, the liquid type identification apparatus further comprising an identification control unit;

the identification control unit being constructed that a pulse voltage is applied to the liquid type identification sensor heater for a predetermined period of time, and the light oil to be identified which temporarily stays within the liquid type identification chamber for a light oil is heated by the heater, and the liquid type is identified with a voltage output difference $V0$, corresponding to a temperature difference between the initial temperature and the peak temperature of the identification liquid temperature sensor.

According to another aspect of the present invention, there is provided a liquid type identification method for a light oil, for identifying the type and distillation properties of a light oil, comprising the steps of:

applying a pulse voltage for a predetermined period of time to a liquid type identification sensor heater comprising a heater and an identification liquid temperature sensor provided in the vicinity of the heater;

heating the light oil to be identified by the heater; and identifying the liquid type with a voltage output difference $V0$, corresponding to a temperature difference between the initial temperature and the peak temperature of the identification liquid temperature sensor.

In the adoption of the above construction, what is required is only to apply pulse voltage for a predetermined period of time. Therefore, the type and distillation properties of a light oil can be identified in an accurate and rapid manner by heating for a short period of time without heating the light oil to a temperature at which the light oil ignites.

Specifically, since the above construction can utilize a correlation between the kinematic viscosity of the light oil and the sensor output, utilizes natural convection, and one pulse applied voltage, the type and distillation properties of a light oil can be identified in an accurate and rapid manner.

Further, the present invention is characterized in that the voltage output difference $V0$ is the difference in voltage between an average initial voltage $V1$ determined by sampling the initial voltage before the application of the pulse voltage by a predetermined number of times and an average peak voltage $V2$ determined by sampling the peak voltage after the application of the pulse voltage by a predetermined number of times, that is, $V0=V2-V1$.

When such a construction is utilized, the voltage output difference $V0$ can be accurately determined based on the average value of a predetermined number of times of sampling for one pulse applied voltage. Therefore, the type and distillation properties of a light oil can be identified in an accurate and rapid manner.

The liquid type identification apparatus for a light oil according to the present invention is characterized in that the identification control unit is constructed so that the type of the light oil is identified using the voltage output difference $V0$ obtained for the light oil to be identified, based on calibration curve data as a correlation between temperature and voltage output difference, for predetermined reference light oils previously stored in the identification control unit.

The liquid type identification method for a light oil according to the present invention is characterized in that the type of the light oil is identified using the voltage output difference $V0$ obtained for the light oil to be identified, based on previously stored calibration curve data as a correlation between temperature and voltage output difference, for predetermined reference light oils.

By such a construction, the type of the light oil can be identified using the voltage output difference $V0$ obtained for the light oil to be identified, based on previously stored calibration curve data as a correlation between temperature and voltage output difference, for predetermined reference light oils. As a result, the type of the light oil can be identified in a more accurate and rapid manner.

Further, the liquid type identification apparatus for a light oil according to the present invention is characterized in that the identification control unit is constructed so that a liquid type voltage output Vout for the voltage output difference $V0$ at a measuring temperature for the light oil to be identified is corrected in a correlation with the output voltage for the voltage output difference at the measuring temperature for a predetermined threshold reference light oil.

Furthermore, the liquid type identification method for a light oil according to the present invention is characterized in that a liquid type voltage output Vout for the voltage output difference $V0$ at a measuring temperature for the light oil to be identified is corrected in a correlation with the output voltage for the voltage output difference at the measuring temperature for a predetermined threshold reference light oil.

By such a construction, a liquid type voltage output Vout for the voltage output difference $V0$ at a measuring temperature for the light oil to be identified is corrected in a correlation with the output voltage for the voltage output difference at the measuring temperature for a predetermined threshold reference light oil. As a result, the influence of the temperature on the voltage output difference $V0$ can be eliminated to impart a more accurate correlation between the liquid type voltage output Vout and the properties of the light oil and, consequently, at the same time, the type of the light oil can be identified in a more accurate and rapid manner.

Furthermore, the present invention is characterized in that the liquid type identification sensor heater is a laminated liquid type identification sensor heater in which a heater and an identification liquid temperature sensor are laminated through an insulating layer.

By such a construction, any mechanically moved mechanism part does not exist. Therefore, malfunction derived from a deterioration with the elapse of time or the presence of foreign matter in the light oil or the like does not occur. Consequently, the liquid type of the light oil can be identified in an accurate and rapid manner.

Furthermore, since the sensor part can be constructed in a very small size, the thermal response is very good and the liquid type of a light oil can be identified with good accuracy. The present invention is further characterized in that the heater and identification liquid temperature sensor in the liquid type identification sensor heater each are constructed so as to come into contact with the light oil to be identified through a metallic fin.

By such a construction, the heater of the liquid type identification sensor heater and the liquid temperature sensor for identification does not come into direct contact with a light oil to be identified. Therefore, malfunction derived from a deterioration with the elapse of time or the presence of foreign matter or the like in the light oil does not occur. Consequently, the liquid type of the light oil can be identified in an accurate and rapid manner.

Furthermore, the present invention is characterized in that the liquid temperature sensor is constructed so as to come into contact with the light oil to be identified through the metallic fin. By such a construction, the liquid temperature sensor does not come into direct contact with a light oil to be identified. Therefore, malfunction derived from a deterioration with the elapse of time or the presence of foreign matter or the like in the light oil does not occur. Consequently, the liquid type of the light oil can be identified in an accurate and rapid manner.

According to the present invention, there is provided a liquid type identification apparatus for an automotive light oil, for identifying the type and distillation properties of the light oil, comprising:

any of the liquid type identification apparatuses for a light oil which is provided within a light oil tank or on the upstream side or downstream side of a light oil pump.

Further, according to the present invention, there is provided a liquid type identification method for an automotive light oil, for identifying the type and distillation properties of the light oil, comprising:

identifying the type and distillation properties of the light oil in a light oil tank or on the upstream side or downstream side of a light oil pump, by using any of the methods for identifying the liquid type of the light oil described above.

By such a construction, in automobiles, the type and distillation properties of a light oil can be identified in an accurate and rapid manner.

According to the present invention, there is provided an automotive exhaust gas reduction apparatus comprising:

any of the above liquid type identification apparatuses for a light oil, which is provided within a light oil tank or on the upstream side or downstream side of a light oil pump; and an ignition timing control unit for regulating ignition timing based on the type of the light oil, which is identified by the liquid type identification apparatus for a light oil.

Further, according to the present invention, there is provided an automotive exhaust gas reduction method, comprising the steps of:

identifying the type and distillation properties of the light oil in a light oil tank or on the upstream side or downstream side of a light oil pump, by using any of the methods for identifying the liquid type of a light oil described above, and regulating an ignition timing based on the type of the light oil which is identified by the liquid type identification apparatus for a light oil.

By such a construction, ignition timing can be adjusted based on the results of identification of the type of a light oil. Therefore, proper ignition timing depending upon the type of a light oil can be provided.

Accordingly, in particular, even when an engine is started, particularly when an engine in which a catalyst device is not in a warmed state is started, the content of HCs in the exhaust gas can be reduced, and, at the same time, fuel consumption can be improved, without causing a reduction in torque.

According to the present invention, there is provided an automotive exhaust gas reduction apparatus comprising:

any of the above liquid type identification apparatuses for a light oil, which is provided within a light oil tank or on the upstream side or downstream side of a light oil pump; and a light oil compression control unit for regulating the compression ratio of the light oil based on the type of the light oil which is identified by the liquid type identification apparatus for a light oil.

Further, according to the present invention, there is provided an automotive exhaust gas reduction method, comprising the steps of:

identifying the type and distillation properties of the light oil in a light oil tank or on the upstream side or downstream side of a light oil pump, by using any of the methods for identifying liquid type of a light oil described above, and regulating the compression ratio of the light oil based on the type of the light oil which is identified by the liquid type identification apparatus for a light oil.

By such a construction, the compression ratio of the light oil can be adjusted based on the results of identification of the type of a light oil. Therefore, proper compression ratio of the light oil depending upon the type of a light oil can be provided.

Accordingly, in particular, even when an engine is started, particularly when an engine in which a catalyst device is not in a warmed state is started, the content of HCs in the exhaust gas can be reduced, and, at the same time, fuel consumption can be improved without causing a reduction in torque.

According to the present invention, what is required is only to apply pulse voltage for a predetermined period of time. Therefore, the type and distillation properties of a light oil can be identified by heating for a short period of time, at the same time, without heating the light oil to a temperature at which the light oil ignites in an accurate and rapid manner.

Specifically, since the above construction can utilize a correlation between the kinematic viscosity of the light oil and the sensor output, utilizes natural convection, and one pulse applied voltage, the type and distillation properties of a light oil can be identified in an accurate and rapid manner.

Further, according to the present invention, since the voltage output difference V0 can be accurately determined based on the average value of a predetermined number of times of sampling for one pulse applied voltage, the type and distillation properties of a light oil can be identified in an accurate and rapid manner.

According to the present invention, since the type of the light oil is identified using the voltage output difference V0 obtained for the light oil to be identified, based on previously stored calibration curve data as a correlation between temperature and voltage output difference, for predetermined reference light oils. Therefore, the type of the light oil can be identified in a more accurate and rapid manner.

According to the present invention, since a liquid type voltage output Vout for the voltage output difference V0 at a measuring temperature for the light oil to be identified is corrected in a correlation with the output voltage for the voltage output difference at the measuring temperature for a predetermined threshold reference light oil. As a result, the influence of the temperature on the voltage output difference V0 can be eliminated to impart a more accurate correlation between the liquid type voltage output Vout and the properties of the light oil. Therefore, the type of the light oil can be identified in a more accurate and rapid manner.

Further, according to the present invention, since any mechanically moved mechanism part does not exist, malfunction derived from a deterioration with the elapse of time or the presence of foreign matter or the like in the light oil does not occur. Consequently, the liquid type of a light oil can be identified in an accurate and rapid manner.

Furthermore, since the sensor part can be constructed in a very small size, the thermal response is very good and the liquid type of a light oil can be identified with good accuracy.

Furthermore, according to the present invention, the heater in the liquid type identification sensor heater, the liquid temperature sensor for identification and the liquid temperature sensor do not come into direct contact with a light oil to be identified. As a result, malfunction derived from a deterioration with the elapse of time or the presence of foreign matter or the like in the light oil does not occur. Consequently, the liquid type of the right oil can be identified in an accurate and rapid manner.

According to the present invention, in automobiles, the type and distillation properties of a light oil can be identified in an accurate and rapid manner and, at the same time, ignition timing can be adjusted based on the results of identification of the type of the light oil. Therefore, proper ignition timing depending upon the type of the light oil can be realized.

Further, according to the present invention, in automobiles, the type and distillation properties of a light oil can be identified in an accurate and rapid manner and, at the same time, the compression ratio can be adjusted based on the results of identification of the light oil. Therefore, proper compression ratio of the light oil depending upon the type of the light oil can be realized.

Thus, the present invention is an excellent invention which exhibits a large number of significant and inherent function and effects, including that, in particular, even when an engine is started, particularly when an engine in which a catalyst device is not in a warmed state is started, the content of HCs in the exhaust gas can be reduced, and, at the same time, fuel consumption can be improved, without causing a reduction in torque.

DETAILED DESCRIPTION OF THE INVENTION

Figure 1:
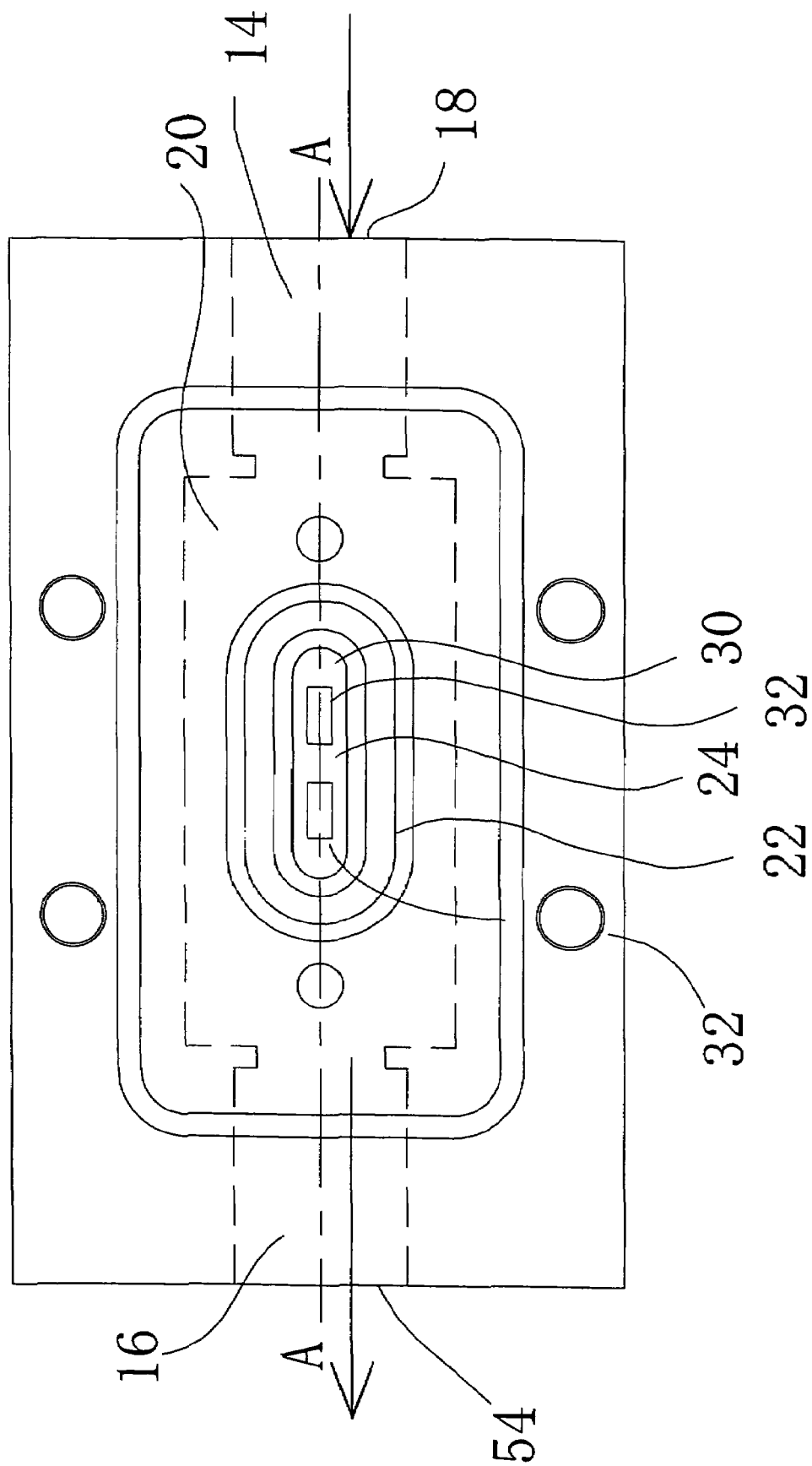
FIG. 1 is a schematic top view of an embodiment of a liquid type identification apparatus for a light oil according to the present invention.
Figure 3:
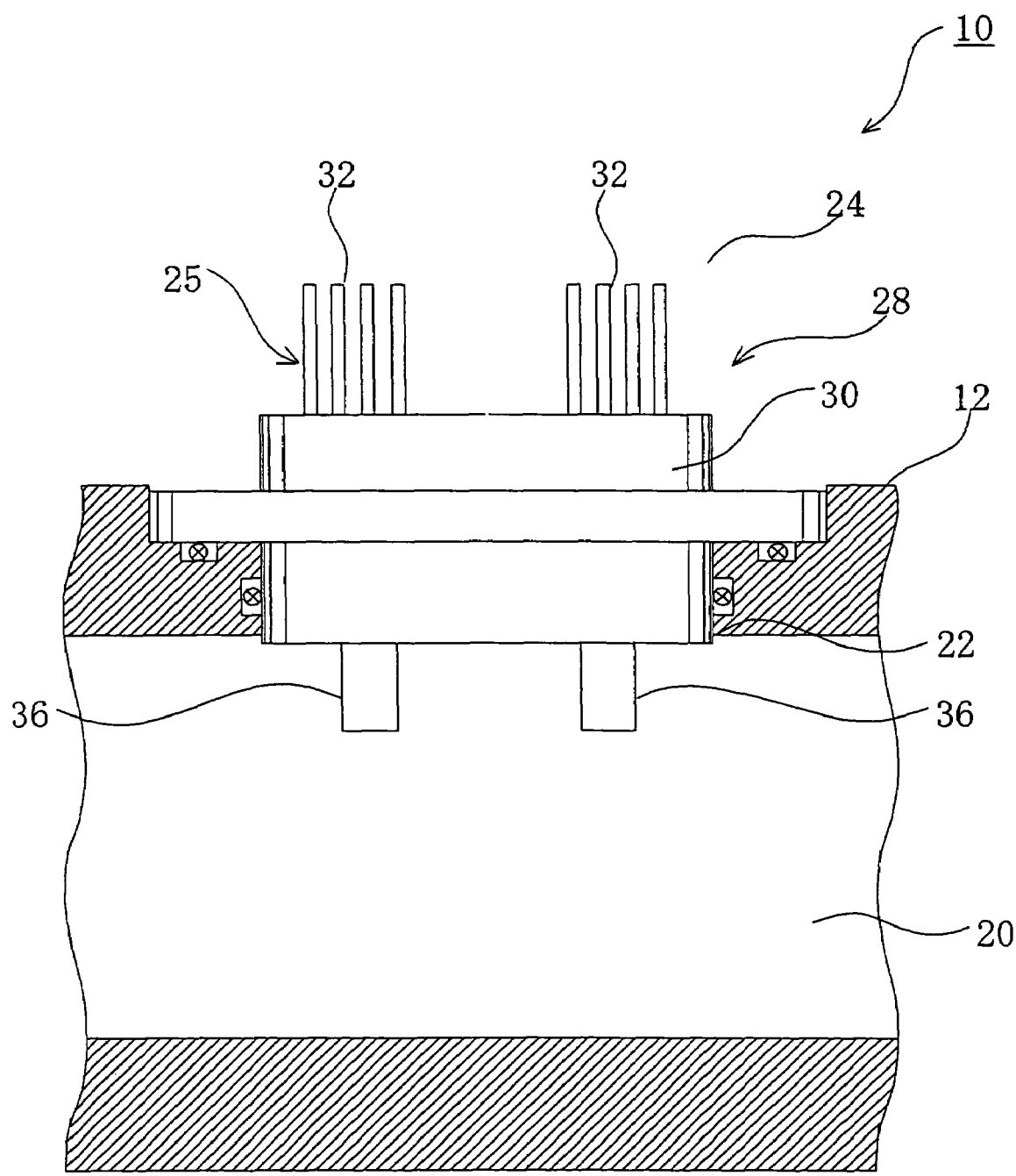
FIG. 3 is a partially enlarged cross-sectional view showing the state of mounting of the liquid type identification sensor shown in FIG. 2.
Figure 4:
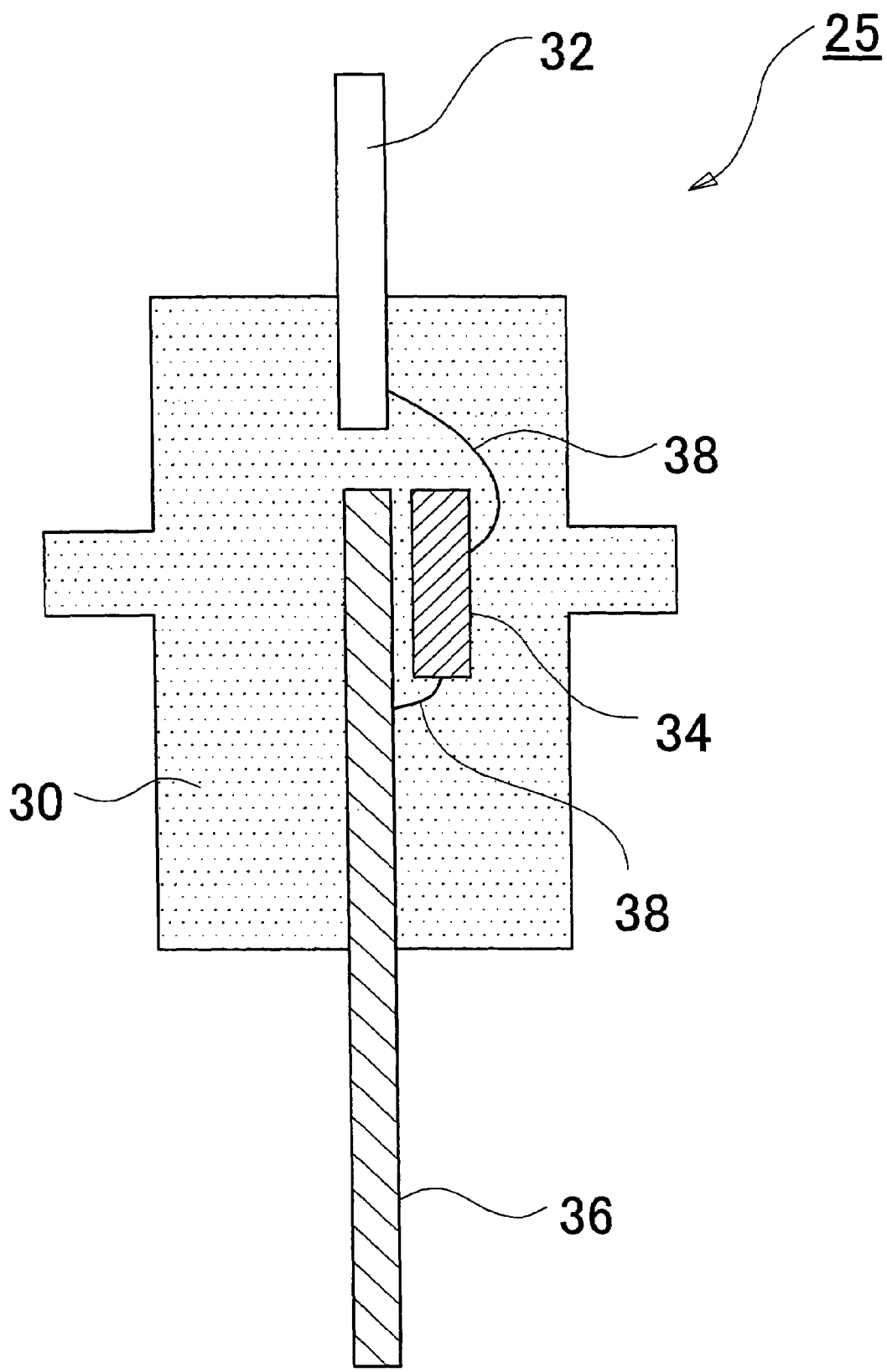
FIG. 4 is a cross-sectional view of a liquid type identification sensor.
Figure 5:
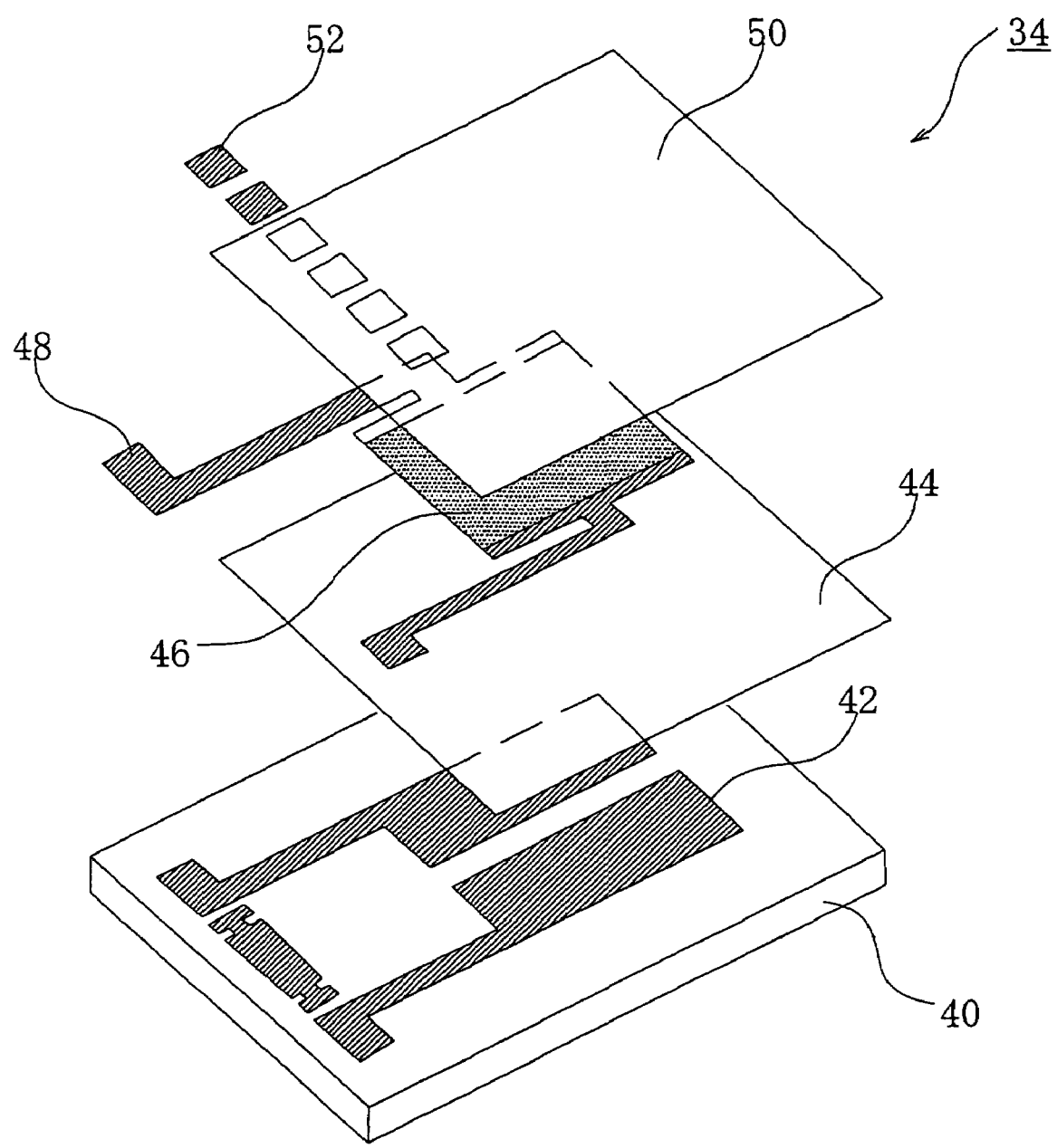
FIG. 5 is a partially enlarged exploded perspective view showing the state of laminating of a thin-film chip part in a liquid type identification sensor.
Figure 6:
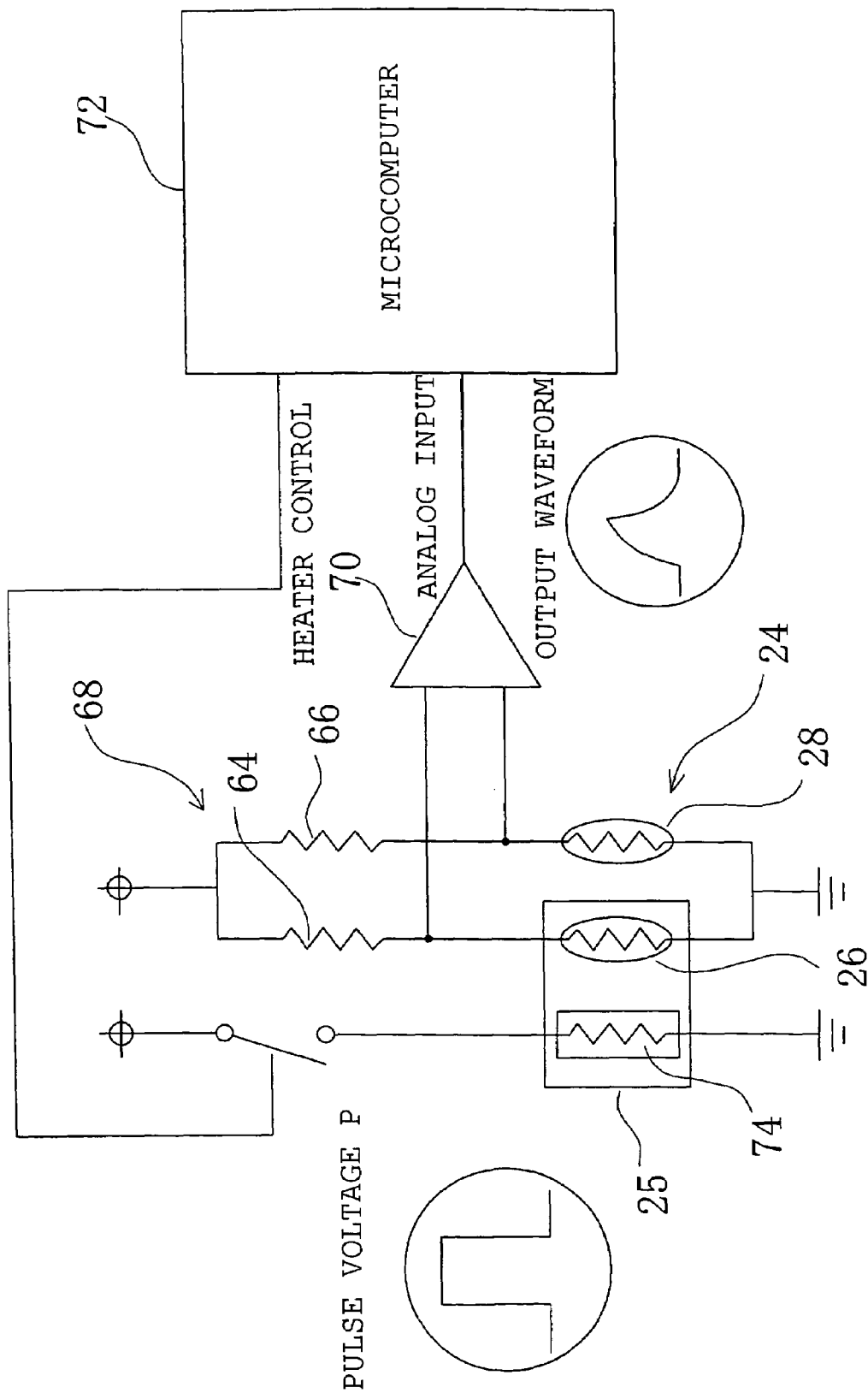
FIG. 6 is a schematic circuit block diagram of an embodiment of a liquid type identification apparatus for a light oil according to the present invention.
Figure 7:
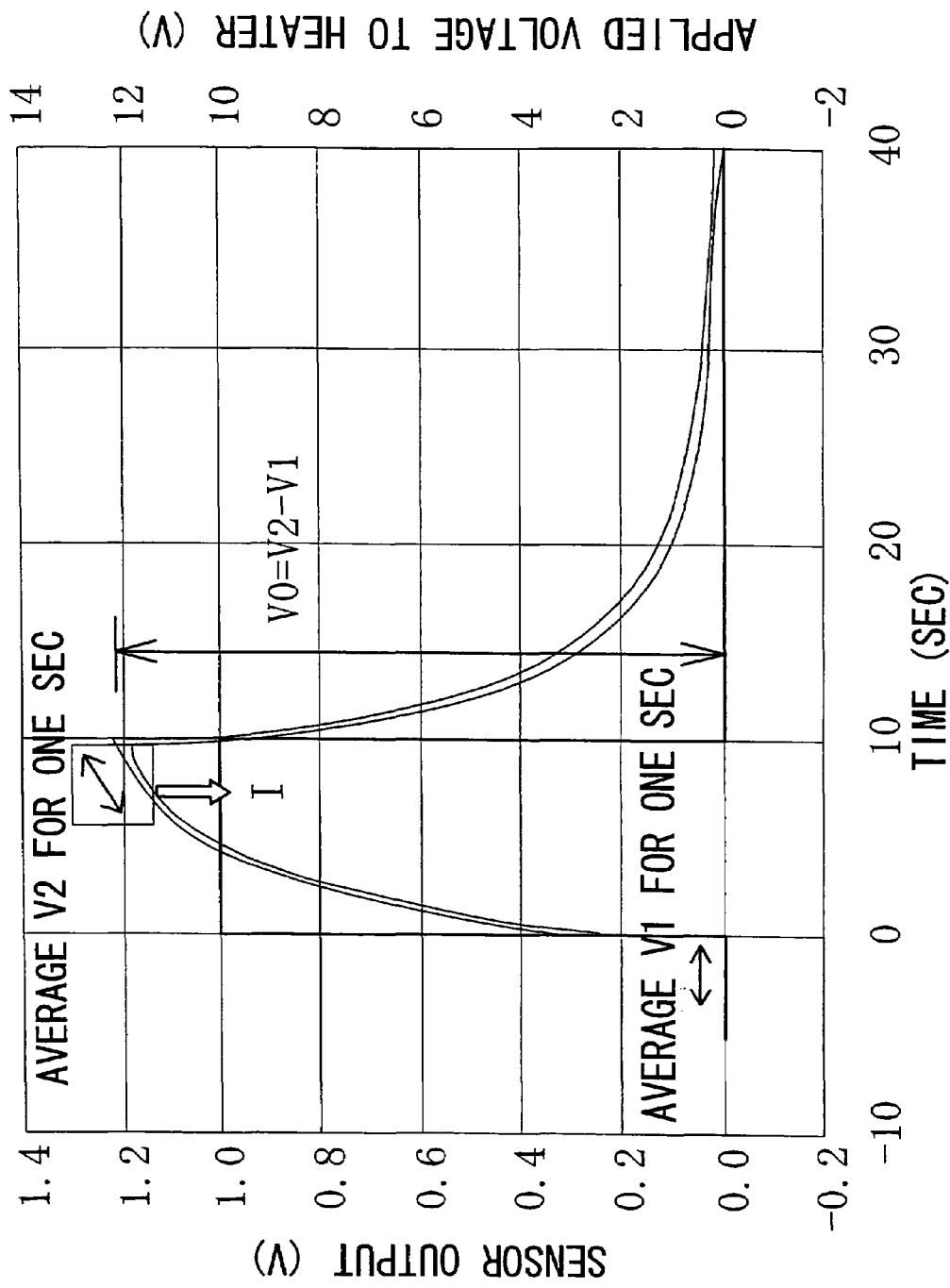
FIG. 7 is a graph showing a time vs. voltage relationship showing a liquid type identification method using a liquid type identification apparatus for a light oil according to the present invention.
Figure 8:
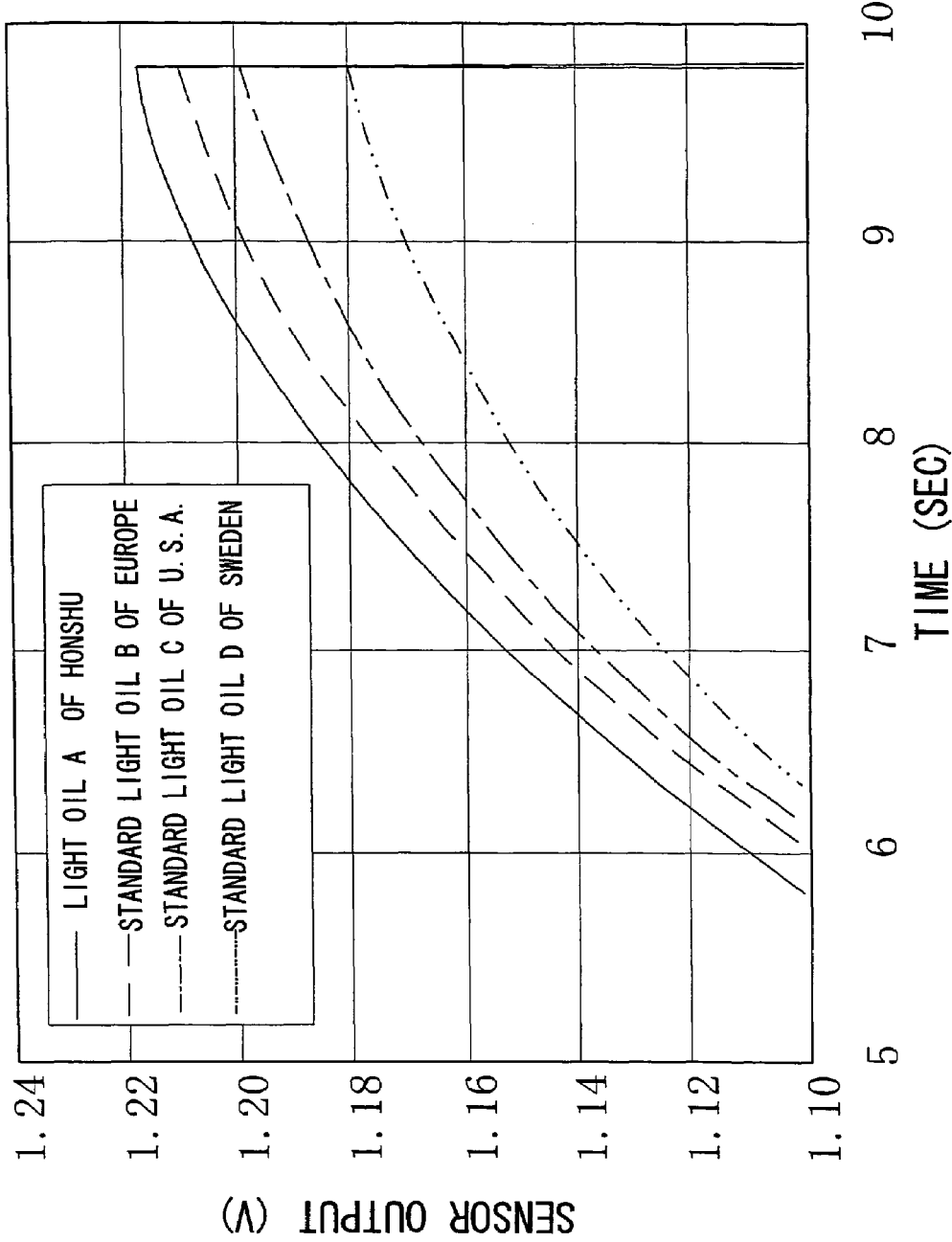
FIG. 8 is a graph of an enlarged I part shown in FIG. 7.
Figure 9:
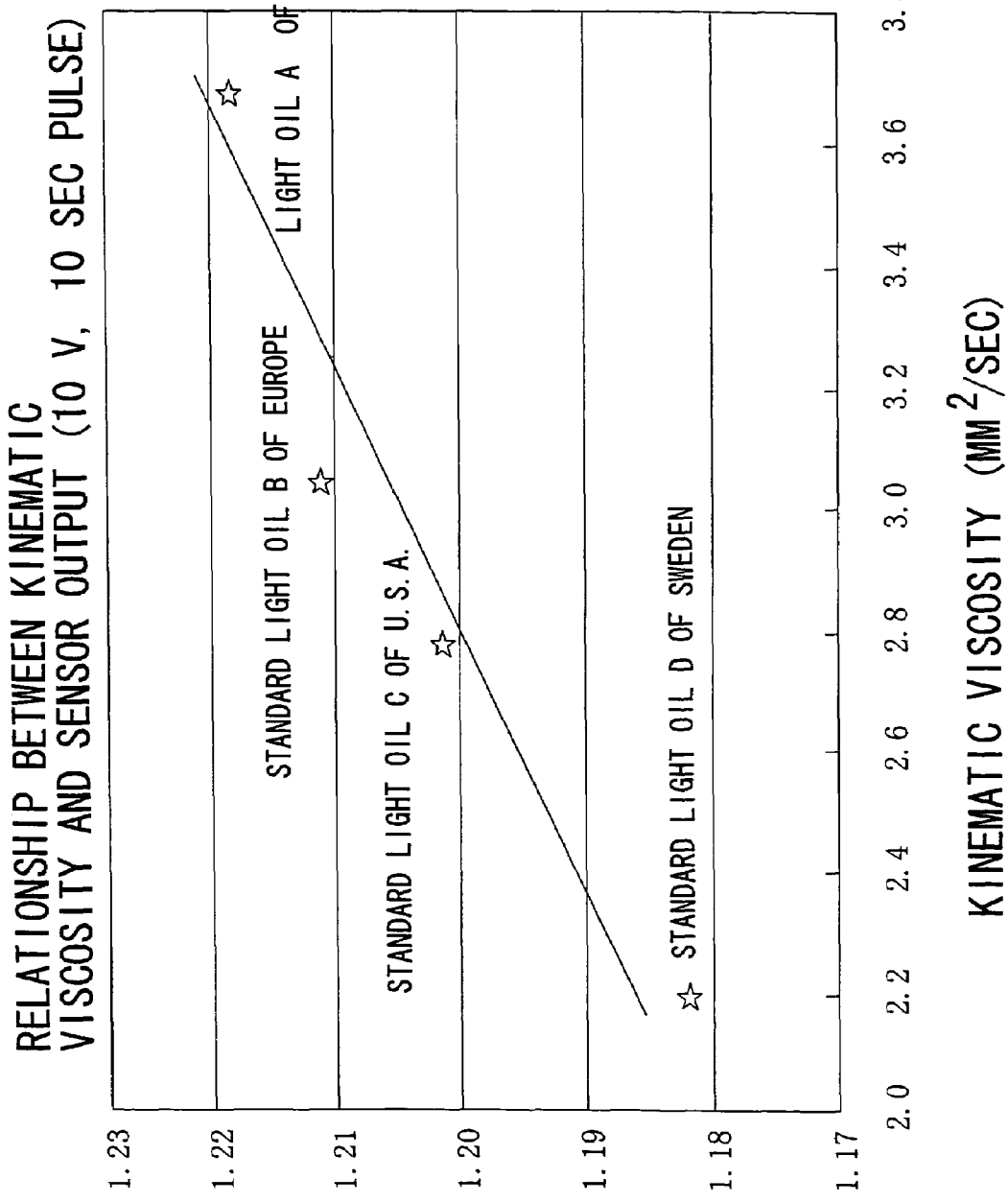
FIG. 9 is a graph showing a kinematic viscosity vs. the sensor output relationship.
Figure 10:
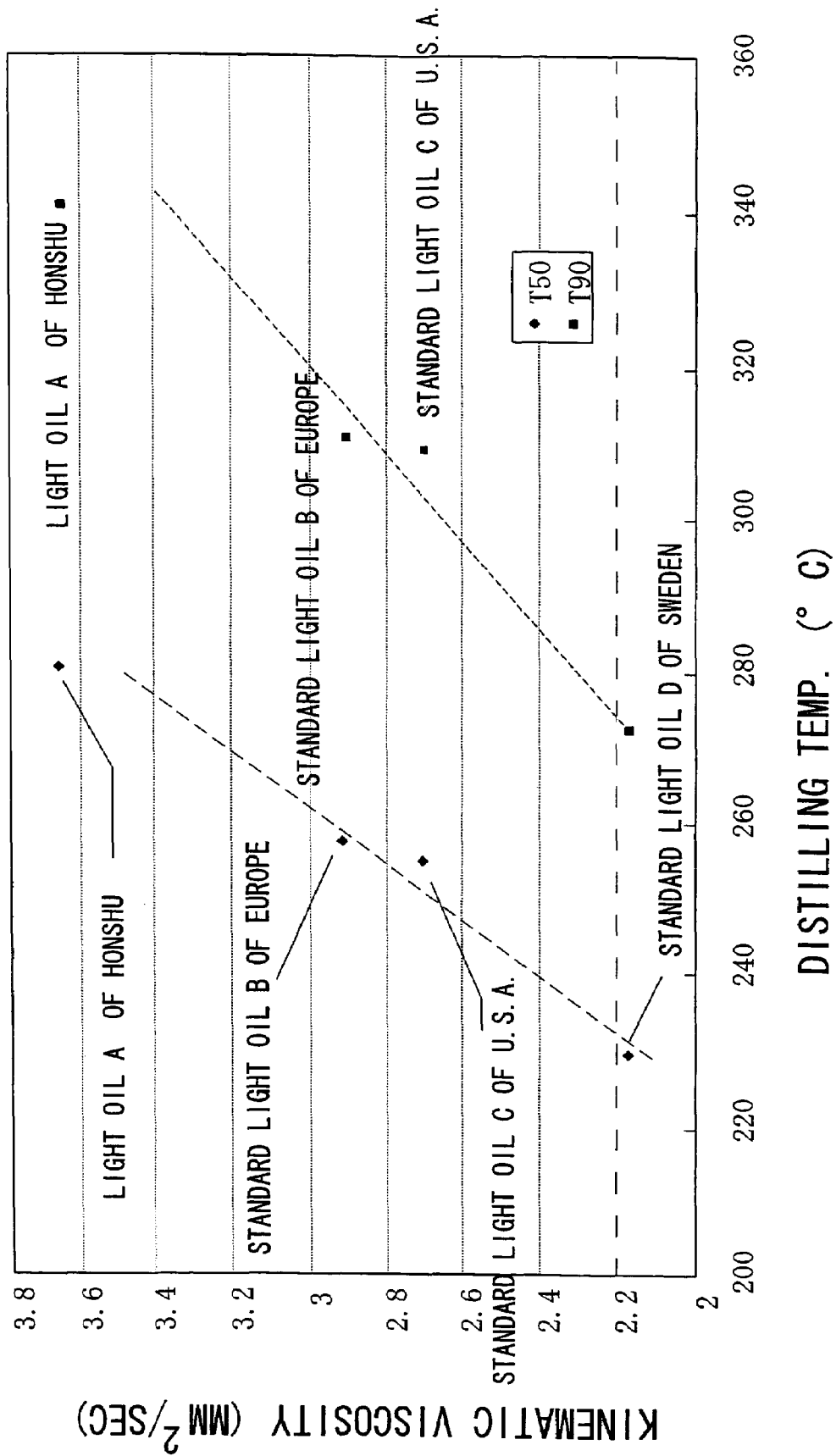
FIG. 10 is a graph showing a kinematic viscosity vs. distillation temperature relationship.
Figure 11:
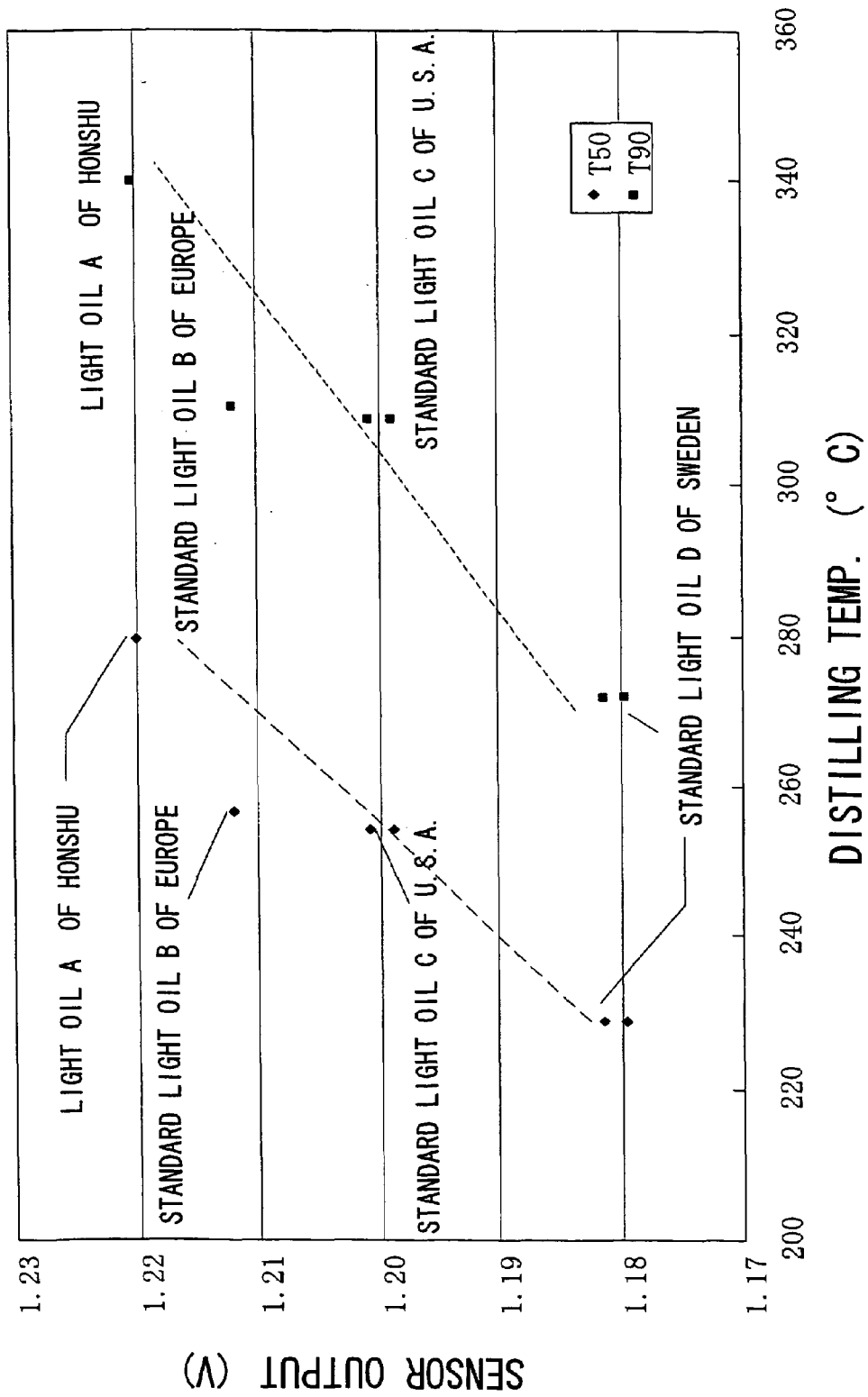
FIG. 11 is a graph showing a sensor output vs. distillation temperature relationship.
Figure 12:
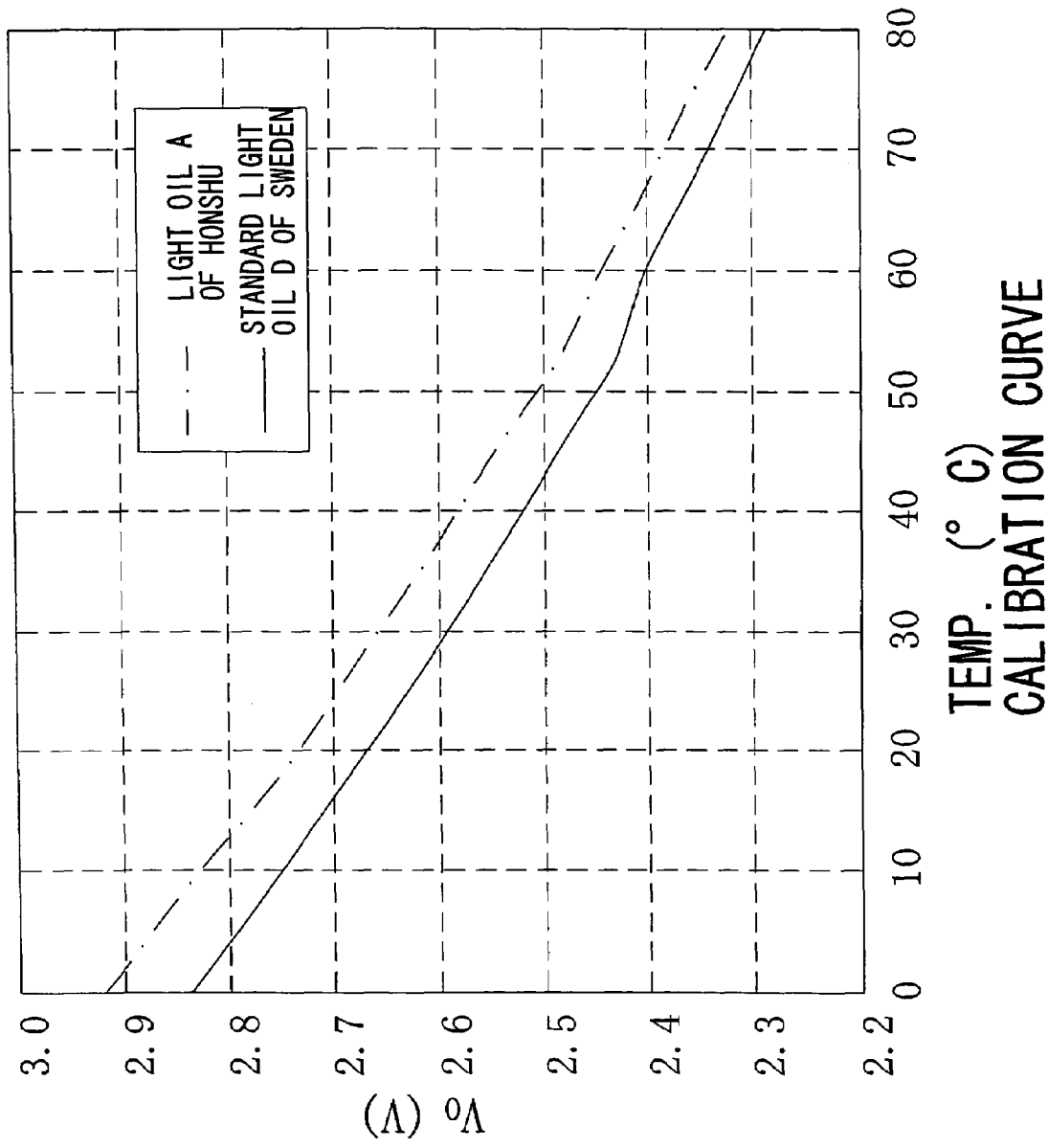
FIG. 12 is a graph showing a calibration curve in a liquid type identification method using a liquid type identification apparatus for a light oil according to the present invention.
Figure 13:
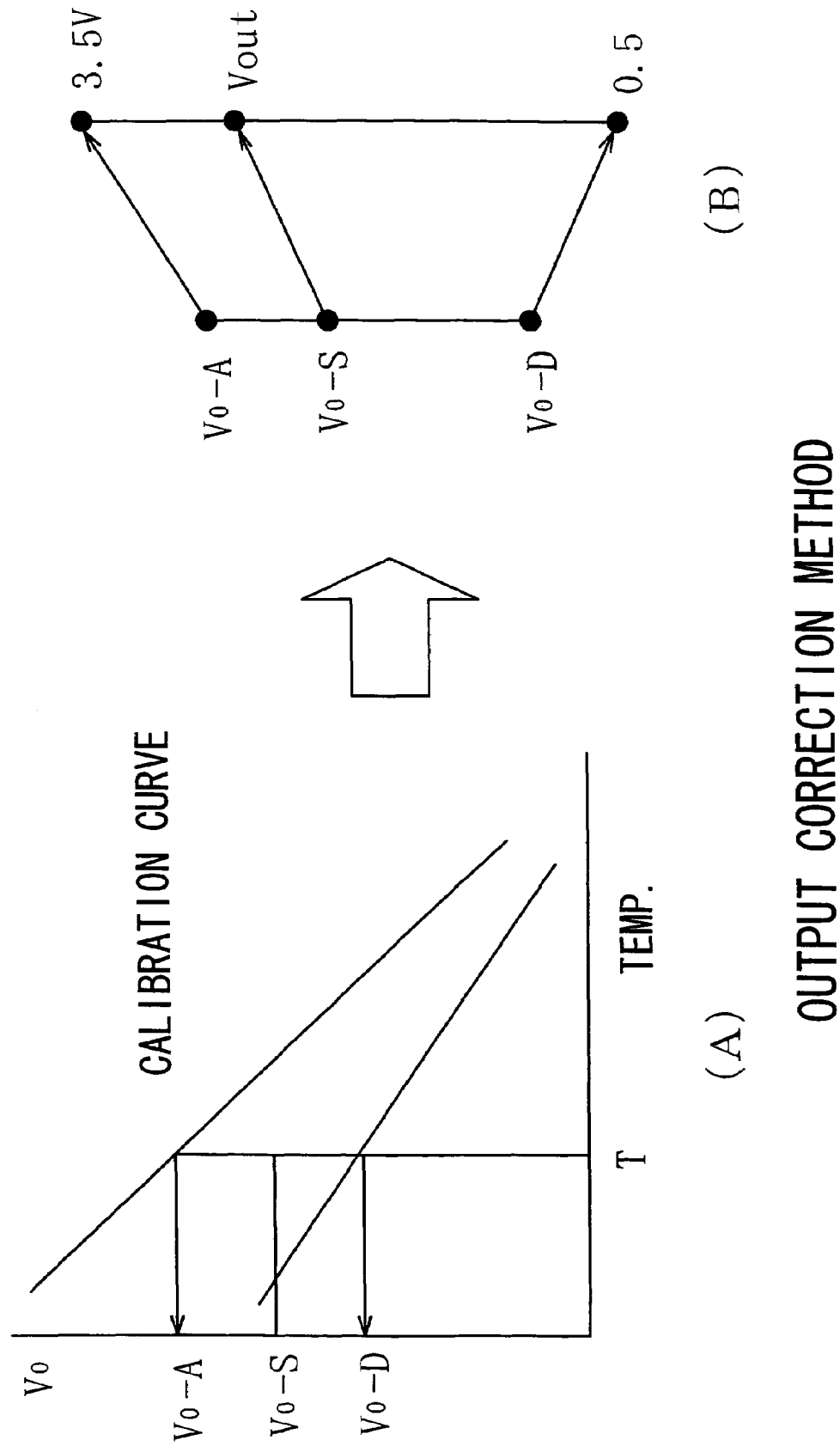
FIG. 13 is a graph showing an output correction method in a liquid type identification method using a liquid type identification apparatus for a light oil according to the present invention.

The mode for carrying out the invention (embodiments) will be described in more detail in conjunction with the accompanying drawings. FIG. 1 is a schematic top view of an embodiment of a liquid type identification apparatus for a light oil according to the present invention, FIG. 2 is a cross-sectional view taken on line A-A of FIG. 1, FIG. 3 is a partially enlarged cross-sectional view showing the state of mounting of the liquid type identification sensor shown in FIG. 2, FIG. 4 is a cross-sectional view of a liquid type identification sensor, FIG. 5 is a partially enlarged exploded perspective view showing the state of laminating of a thin-film chip part in a liquid type identification sensor, FIG. 6 is a schematic circuit block diagram of an embodiment of a liquid type identification apparatus for a light oil according to the present invention, FIG. 7 is a graph showing a time vs. voltage relationship showing a liquid type identification method using a liquid type identification apparatus for a light oil according to the present invention, FIG. 8 is a graph of an enlarged I part shown in FIG. 7, FIG. 9 is a graph showing a kinematic viscosity vs. sensor output relationship, FIG. 10 is a graph showing a kinematic viscosity vs. distillation temperature relationship, FIG. 11 is a graph showing a sensor output vs. distillation temperature relationship, FIG. 12 is a graph showing a calibration curve in a liquid type identification method using a liquid type identification apparatus for a light oil according to the present invention, and FIG. 13 is a graph showing an output correction method in a liquid type identification method using a liquid type identification apparatus for a light oil according to the present invention.

Figure 2:
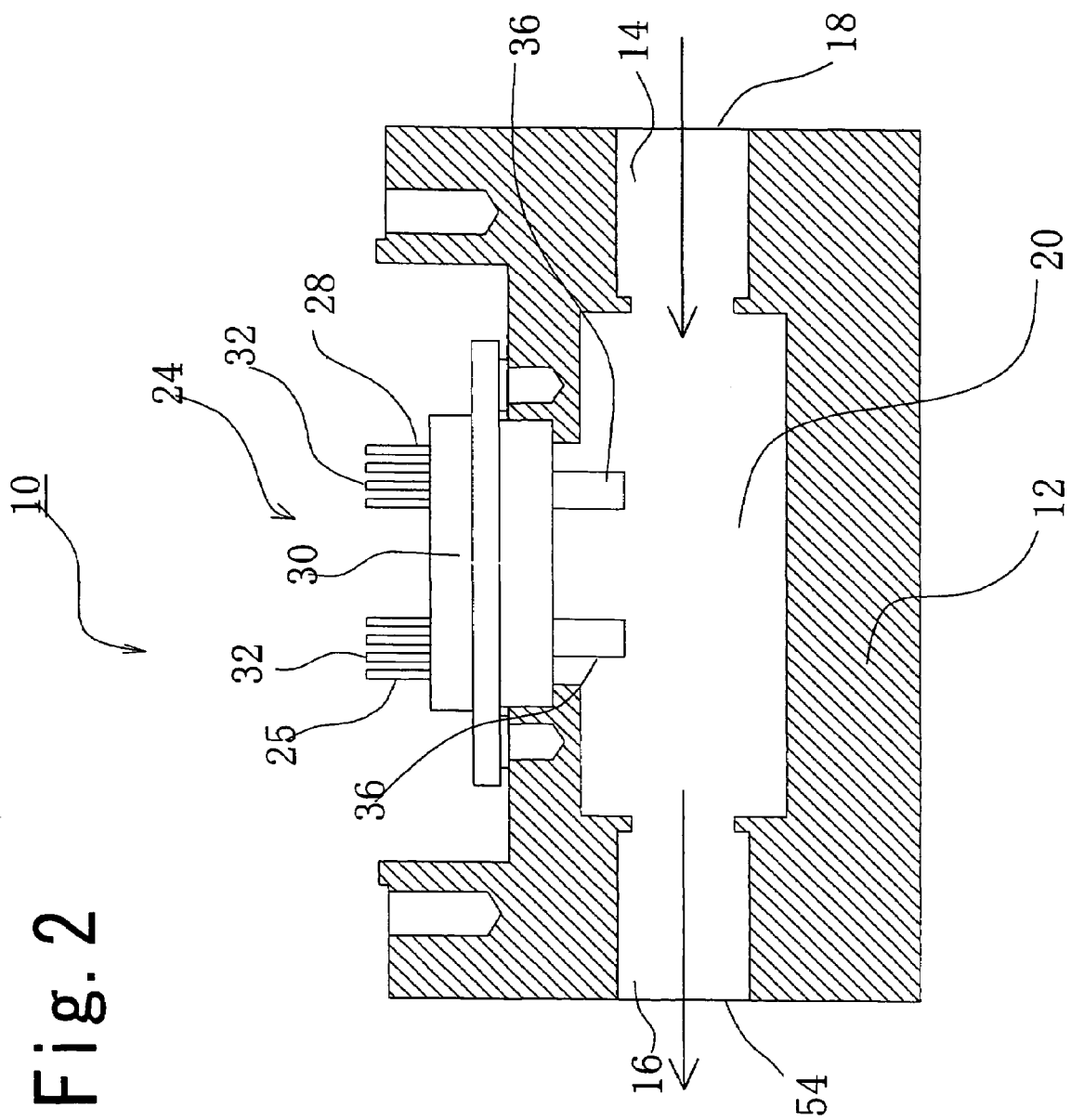
FIG. 2 is a cross-sectional view taken on line A-A of FIG. 1.

As shown in FIGS. 1 and 2, a liquid type identification apparatus 10 for a light oil according to the present invention comprises a liquid type identification apparatus body 12, and a first passage 14 and a second passage 16 provided within the liquid type identification apparatus body 12.

As indicated by an arrow shown in FIG. 1, a light oil is introduced through a light oil inflow port 18, is passed through a first passage 14, and temporarily stays within a light oil liquid type identification chamber 20. In this light oil liquid type identification chamber 20, a substantially track-shaped liquid type identification sensor opening part 22 is provided on its upper part.

As shown in FIG. 2, a liquid type identification sensor 24 is mounted in the liquid type identification sensor opening part 22.

As shown in FIG. 3, the liquid type identification sensor 24 comprises a liquid type identification sensor heater 25 and a liquid temperature sensor 28 disposed by a given distance from the liquid type identification sensor heater 25. The liquid type identification sensor heater 25 and the liquid temperature sensor 28 are formed integrally with a mold resin 30.

Further, as shown in FIG. 4, the liquid type identification sensor heater 25 comprises lead electrodes 32 and a thin-film chip part 34. In the liquid type identification sensor heater 25, metallic fins 36 are provided. The metallic fins 36 are protruded from the mold resin 30 into the liquid type identification chamber 20 for a light oil through the opening part 22 for a liquid type identification sensor so as to come into direct contact with the light oil to be identified. These lead electrodes 32, thin-film chip part 34, and fins 36 are electrically connected to each other through a bonding wire 38.

On the other hand, the liquid temperature sensor 28 has the same construction as the liquid type identification sensor heater 25 and comprises a lead electrode 32, a thin-film chip part 34, fins 36 and a bonding wire 38.

As shown in FIG. 5, the thin-film chip part 34 comprises a thin-film chip comprising, for example, a substrate 40 formed of $Al_2O_3$, a temperature sensor (a temperature detector) 42 formed of Pt, an interlayer insulation film 44 formed of $SiO_2$, a heater (a heating element) 46 formed of $TaSiO_2$, a heating element electrode 48 formed of Ni, a protective film 50 formed of $SiO_2$, and an electrode pad 52 formed of Ti/Au laminated in that order.

The thin-film chip part 34 in the liquid temperature sensor 28 also has the same structure, except that only the temperature sensor (temperature detector) 42 is allowed to act without allowing the heater (heating element) 46 to act.

After the type and distillation properties of the light oil to be identified are identified with this liquid type identification sensor 24, the identified light oil is discharged from a liquid type identification chamber 20 for a light oil, is passed through a second passage 16, and is discharged into the outside of the apparatus through a light oil discharge port 54. In FIGS. 1 and 2, a circuit substrate member connected to the liquid type identification sensor 24 and a lid member covering this are omitted.

In the liquid type identification apparatus 10 for a light oil according to the present invention, the circuit construction is as shown in FIG. 6.

In FIG. 6, a liquid temperature sensor 26 for identification in a liquid type identification sensor heater 25 of a liquid type identification sensor 24 is connected to a liquid temperature sensor 28 through two resistors 64, 66 to constitute a bridge circuit 68. The output of the bridge circuit 68 is connected to the input of an amplifier 70. The output of this amplifier 70 is connected to the input of a computer 72 constituting an identification control unit.

A heater 74 in the liquid type identification sensor heater 25 is constructed so that the applied voltage is controlled by the control of the computer 72.

In the liquid type identification apparatus 10 for a light oil having the above construction, the liquid type of the light oil is identified as follows.

First of all, a light oil to be identified is allowed to flow through a light oil inflow port 18 in a first passage 14 in the liquid type identification apparatus 10 for a light oil and is allowed to temporarily stay in a liquid type identification chamber 20 for a light oil.

As shown in FIGS. 6 and 7, a pulse voltage P is applied to the heater 74 in the liquid type identification sensor heater 25 for a predetermined period of time, for example, for 10 sec in the case of this embodiment, by controlling the computer 72. Then, a change in temperature of the analog output of a sensing part, that is, a sensor bridge circuit 68 is measured as shown in FIG. 6.

That is, as shown in FIG. 7, a voltage difference in a sensor bridge circuit 68 before the application of a pulse voltage P to the heater 74 in the liquid type identification sensor heater 25 is sampled a predetermined number of times in one sec, for example, 256 times in the case of this embodiment, and the average value thereof is determined as an average initial voltage V1. The value of the average initial voltage V1 corresponds to the initial temperature of the liquid temperature sensor 26 for identification.

Thereafter, as shown in FIG. 7, a predetermined pulse voltage P (in this embodiment, a voltage of 10 V for 10 sec) is applied to the heater 74 in the liquid type identification sensor heater 25. Next, after a predetermined period of time (in this embodiment, after 9 sec), the peak voltage is sampled a predetermined number of times (in this embodiment, 256 times for one sec), and the average of sampled data is determined as an average peak voltage V2. This average peak voltage V2 corresponds to a peak temperature of the liquid temperature sensor 26 for identification.

An voltage output difference V0 is obtained from the voltage difference between an average initial voltage V1 and an average peak voltage V2, that is, V0=2−V1.

In a preferred embodiment, the difference in properties between light oils can be identified by heating the heater 74 in the liquid type identification sensor heater 25 at 50 to 400 mW, preferably 250 mW, and, 1 to 50 sec, preferably 10 sec after the initiation of the heat generation, a change in temperature of the liquid temperature sensor 26 for identification is measured at a voltage output difference V0.

Specifically, as is apparent from a graph shown in FIG. 8 which is an enlarged I part shown in FIG. 7, the test oils are different from each other in the voltage output difference V0 10 sec after the initiation of the heat generation as follows:

light oil A of Honshu . . . 1.20 V standard light oil B of Europe . . . 1.21 V standard light oil C of U.S.A. . . . 1.20 V Standard light oil D of Sweden . . . 1.18 V Accordingly, the liquid type and distillation properties for light oils can be identified based on data which have been previously stored in the computer 72 constituting the identification control unit.

The above liquid type identification method for a light oil utilizes natural convection and such a principle that the kinematic viscosity of the light oil is correlated with the sensor output.

Specifically, as shown in FIG. 9, there is a correlation between the kinematic viscosity and the sensor output, and, as shown in FIG. 10, there is also a correlation between the kinematic viscosity and the distilling temperature. As a result, as shown in FIG. 11, a correlation exists between the sensor output and the distilling temperature. In the liquid type identification apparatus according to the present invention, as described above, the liquid type and distillation properties for light oils can be identified by taking advantage of this relationship.

Further, the liquid type and distillation properties of light oils can be identified in a more accurate and rapid manner by the following method.

Specifically, as shown in FIG. 12, for predetermined reference light oils, for example, for the heaviest (difficult to evaporate) light oil A of Honshu and the lightest (easy to evaporate) standard light oil D of Sweden in this embodiment, calibration curve data for a temperature vs. voltage output difference correlation are previously obtained and are stored in the computer 72 constituting the identification control unit.

Thereafter, a proportional calculation is carried out with the computer 72 based on the calibration curve data, and the type of the light oil is identified based on the voltage output difference V0 obtained for the light oil to be identified.

Specifically, as shown in FIG. 13, the liquid type voltage output Vout for the voltage output difference V0 at the measuring temperature T of the light oil to be identified is correlated with the output voltage for the voltage output difference at the measuring temperature for a predetermined threshold reference light oil (in this embodiment, light oil A of Honshu and standard light oil D of Sweden) for correction.

Specifically, as shown in FIG. 13 (A), based on the calibration curve data, at a temperature T, the voltage output difference V0-A for light oil A of Honshu, the voltage output difference V0-D for standard light oil D of Sweden, and the voltage output difference V0-S for the light oil to be identified are obtained.

As shown in FIG. 13 (B), a correlation with the properties of a light oil can be established by bringing the liquid type output of the threshold reference light oil in this case to a predetermined voltage, that is, by, in this embodiment, bringing the liquid type output of light oil A of Honshu to 3.5 V and bringing the liquid type output of standard light oil D of Sweden to 0.5 V, and obtaining the liquid type voltage output Vout of the light oil to be identified.

The liquid type of the light oil can be identified in an accurate and rapid (instantaneous) manner by previously comparing the liquid type voltage output Vout of this light oil to be identified with the data stored in the computer 72 based on the calibration curve data.

Figure 17:
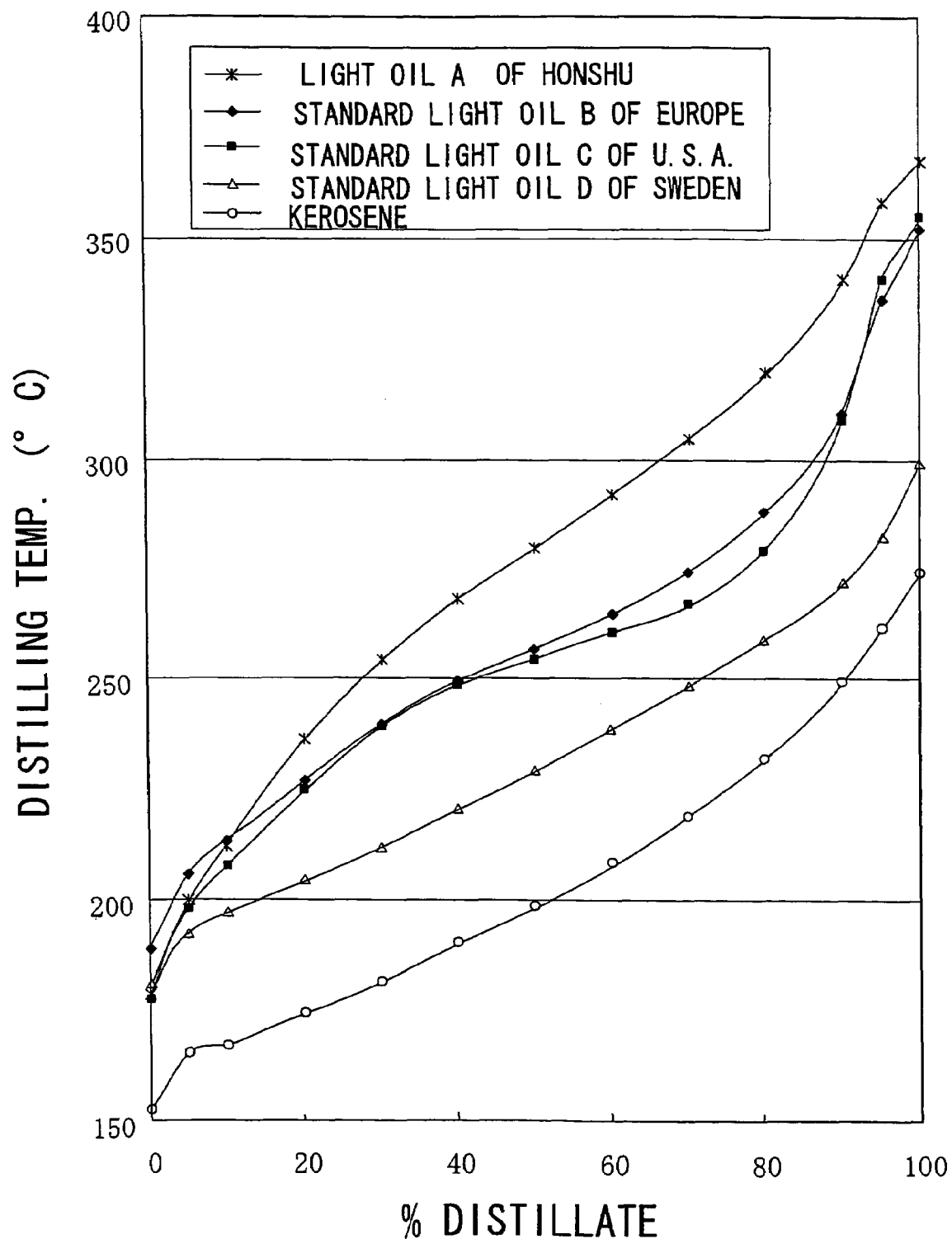
FIG. 17 is a graph showing distillation properties of a light oil.

Further, regarding the liquid type identification method for a light oil, in the distillation properties of light oils shown in FIG. 17, distillation properties T30 to T70 have been found to provide a better correlation and thus are preferred.

Figure 14:
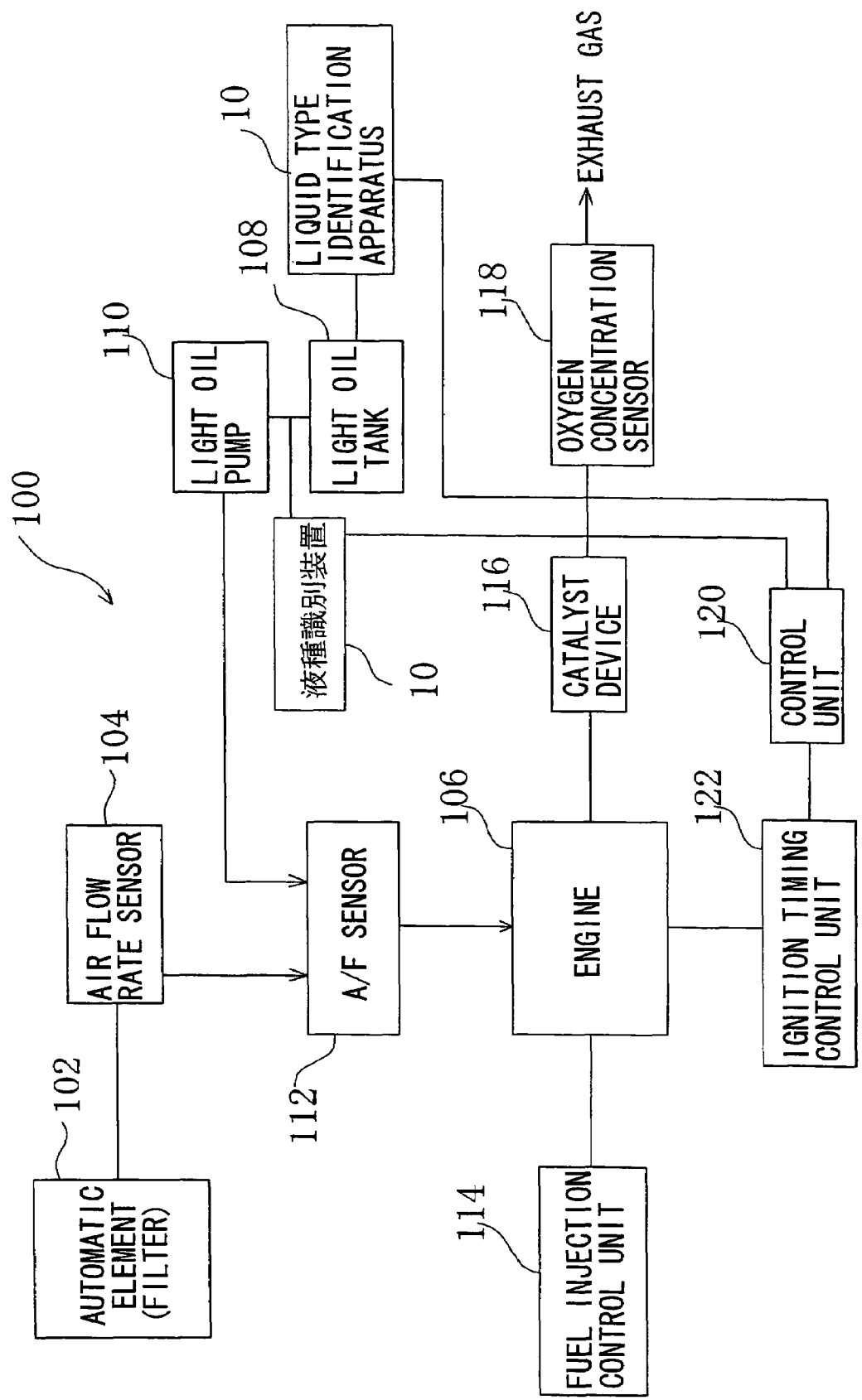
FIG. 14 is the same schematic diagram as FIG. 16, illustrating an embodiment in which the apparatus 10 for identifying the liquid type of a light oil having a such structure is applied to an automobile system.
Figure 16:
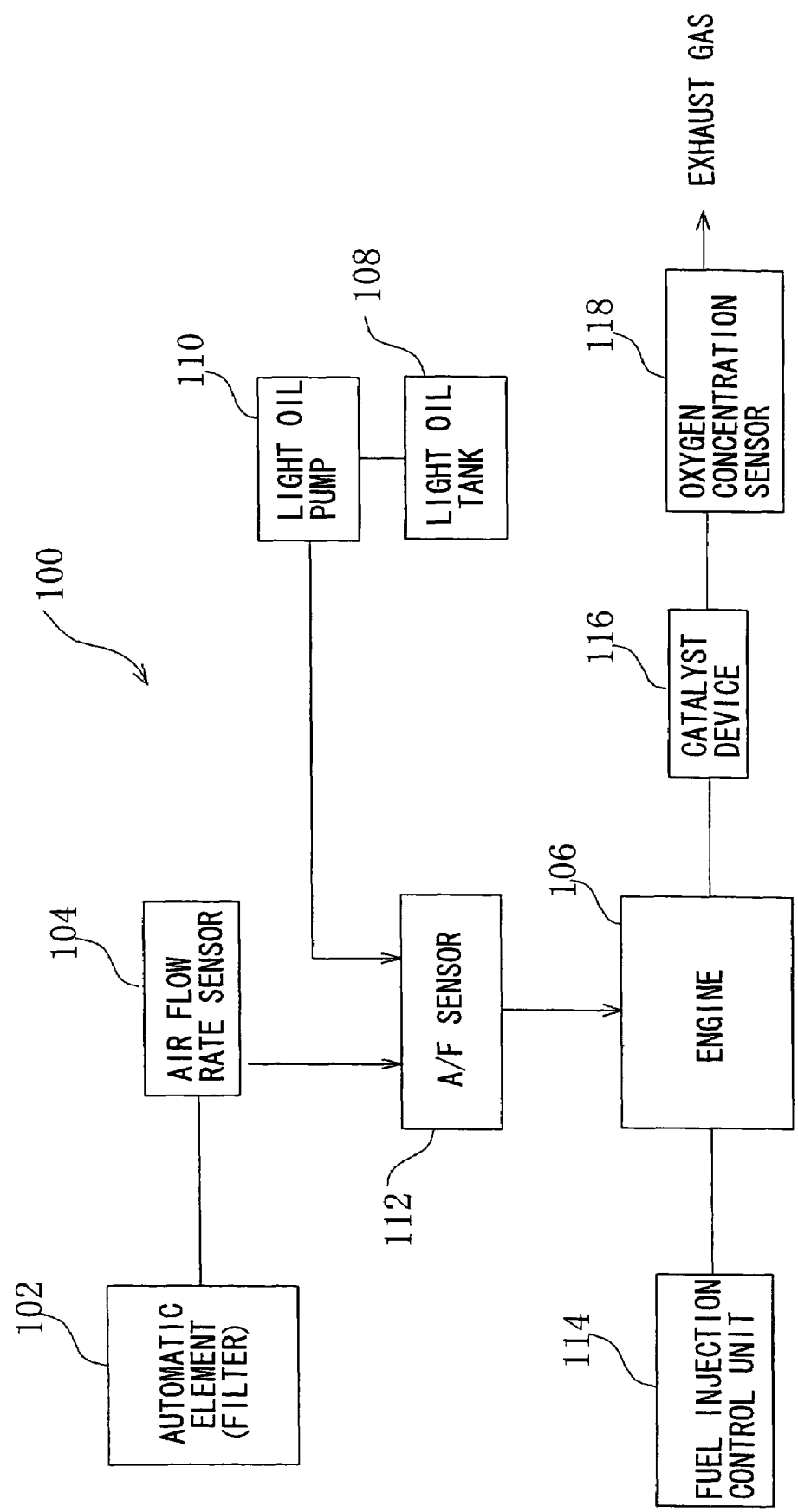
FIG. 16 is a schematic diagram of a conventional automobile system.

FIG. 14 is the same schematic diagram as FIG. 16, illustrating an embodiment in which the apparatus 10 for identifying the liquid type of a light oil having such a structure is applied to an automobile system.

The same component as those in FIG. 16 have the same reference numerals, and the detailed description thereof is omitted.

In this automobile system 100, a liquid type identification apparatus 10 for a light oil is provided within a light oil tank 108 or on the upstream side of a light oil pump 110.

This automobile system 100 is constructed so that the liquid type of the light oil within the light oil tank 108 or on the upstream side or downstream side of the light oil pump 110 (in this embodiment, the case of the upstream side is shown for convenience of explanation) is identified by the liquid type identification apparatus 10 for a light oil. Then, and ignition timing is adjusted by an ignition timing control unit 122 through the control of a control unit 120 depending upon the type of the light oil.

Specifically, for example, when light (easy to evaporate) Standard light oil D of Sweden has been identified, the ignition timing is controlled to earlier one. To the contrary, when heavy (difficult to evaporate) Light oil A of Honshu has been identified, the ignition timing is controlled to delayed one.

Accordingly, in particular, even when an engine is started, particularly when an engine in which a catalyst device is not in a warmed state is started, the content of HCs in the exhaust gas can be reduced, and, at the same time, fuel consumption can be improved, without causing a reduction in torque.

Figure 15:
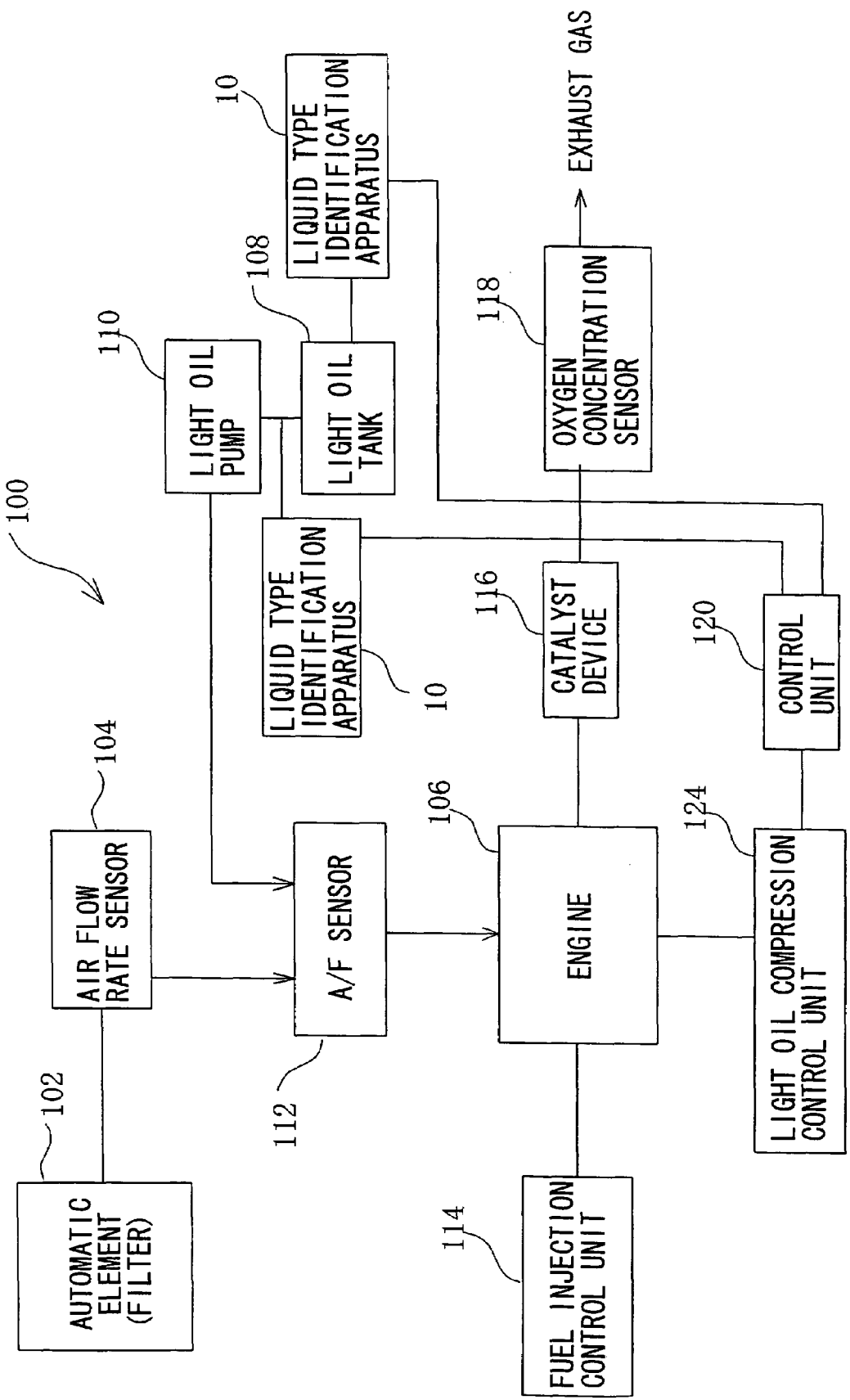
FIG. 15 is the same schematic diagram as FIG. 16 illustrating an embodiment in which the apparatus 10 for identifying the liquid type of a light oil having a such structure is applied to an automobile system.

FIG. 15 is the same schematic diagram as FIG. 16, illustrating an embodiment in which the apparatus 10 for identifying the liquid type of a light oil having such a structure is applied to an automobile system.

The same component as those in FIG. 16 have the same reference numerals, and the detailed description thereof is omitted.

In this automobile system 100, a liquid type identification apparatus 10 for a light oil is provided within a light oil tank 108 or on the upstream side of a light oil pump 110.

This automobile system 100 is constructed so that the liquid type of the light oil within the light oil tank 108 or on the upstream side or downstream side of the light oil pump 110 (in this embodiment, the case of the upstream side is shown for convenience of explanation) is identified by the liquid type identification apparatus 10 for a light oil. Then, the compression ratio of the light oil is regulated by a light oil compression control unit 124 through the control of a control unit 120 depending upon the type of the light oil.

Specifically, for example, when light (easy to evaporate) Standard light oil D of Sweden has been identified, the compression ratio is controlled so as to be lowered. On the contrary, when heavy (difficult to evaporate) Light oil A of Honshu has been identified, the compression ratio is controlled so as to be enhanced.

Accordingly, in particular, even when an engine is started, particularly when an engine in which a catalyst device is not in a warmed state is started, the content of HCs in the exhaust gas can be reduced, and, at the same time, fuel consumption can be improved, without causing a reduction in torque.

Preferred embodiments of the present invention have been described above. However, it should be noted that the present invention is not limited to these preferred embodiments, and various variations and modifications, for example, proper changing of pulse voltage P and number of times of sampling, are possible without departing from the object of the invention.

According to the present invention, the type of light oils used, for example, in automobiles, agricultural machines, and plants, can be identified.

The invention claimed is:

1. A liquid type identification apparatus for a light oil, for identifying the type and distillation properties of a light oil, comprising:
   a liquid type identification chamber for a light oil, for allowing a light oil to be identified, which has been introduced into a liquid type identification apparatus body, to temporarily stay therein;
   a liquid type identification sensor heater provided within the light oil type identification chamber; and
   a liquid temperature sensor spaced by a given distance from the liquid type identification sensor heater and provided within the light oil type identification chamber, the liquid type identification sensor heater comprising a heater and an identification liquid temperature sensor provided in the vicinity of the heater, the liquid type identification apparatus further comprising an identification control unit;

the identification control unit being constructed that a pulse voltage is applied to the liquid type identification sensor heater for a predetermined period of time, and the light oil to be identified which temporarily stays within the liquid type identification chamber for a light oil is heated by the heater, and the liquid type is identified with a voltage output difference V0, corresponding to a temperature difference between the initial temperature and the peak temperature of the identification liquid temperature sensor.

2. The liquid type identification apparatus for a light oil according to claim 1, characterized in that the voltage output difference V0 is the difference in voltage between an average initial voltage V1 determined by sampling the initial voltage before the application of the pulse voltage by a predetermined number of times and an average peak voltage V2 determined by sampling the peak voltage after the application of the pulse voltage by a predetermined number of times, that is, V0=V2−V1.

3. The liquid type identification apparatus for a light oil according to claim 1, characterized in that the identification control unit is constructed so that the type of the light oil is identified using the voltage output difference V0 obtained for the light oil to be identified, based on calibration curve data as a correlation between temperature and voltage output difference, for predetermined reference light oils previously stored in the identification control unit.

4. The liquid type identification apparatus for a light oil according to claim 1, characterized in that the identification control unit is constructed so that a liquid type Vout for the voltage output difference V0 at a measuring temperature for the light oil to be identified is corrected in a correlation with the output voltage for the voltage output difference at the measuring temperature for a predetermined threshold reference light oil.

5. The liquid type identification apparatus for a light oil according to claim 1, characterized in that the liquid type identification sensor heater is a laminated liquid type identification sensor heater in which a heater and an identification liquid temperature sensor are laminated through an insulating layer.

6. The liquid type identification apparatus for a light oil according to claim 1, characterized in that the heater and identification liquid temperature sensor in the liquid type identification sensor heater each are constructed so as to come into contact with the light oil to be identified through a metallic fin.

7. The liquid type identification apparatus for a light oil according to claim 1, characterized in that the liquid temperature sensor is constructed so as to come into contact with the light oil to be identified through the metallic fin.

8. The liquid type identification apparatus for an automotive light oil, for identifying the type and distillation properties of the light oil, comprising:

the liquid type identification apparatus for a light oil according to claim 1 which is provided within a light oil tank or on the upstream side or downstream side of a light oil pump.

9. An automotive exhaust gas reduction apparatus comprising:

a liquid type identification apparatus for a light oil according to claim 1, which is provided within a light oil tank or on the upstream side or downstream side of a light oil pump; and an ignition timing control unit for regulating ignition timing based on the type of the light oil, which is identified by the liquid type identification apparatus for a light oil.

10. An automotive exhaust gas reduction apparatus comprising:

a liquid type identification apparatus for a light oil according to claim 1, which is provided within a light oil tank or on the upstream side or downstream side of a light oil pump; and a light oil compression control unit for regulating the compression ratio of the light oil based on the type of the light oil which is identified by the liquid type identification apparatus for a light oil.

11. A liquid type identification method for a light oil, for identifying the type and distillation properties of a light oil, comprising the steps of:

applying a pulse voltage for a predetermined period of time to a liquid type identification sensor heater comprising a heater and an identification liquid temperature sensor provided in the vicinity of the heater;

heating the light oil to be identified by the heater; and identifying the liquid type with a voltage output difference V0, corresponding to a temperature difference between the initial temperature and the peak temperature of the identification liquid temperature sensor.

12. The liquid type identification method for a light oil according to claim 11, characterized in that the voltage output difference V0 is the difference in voltage between an average initial voltage V1 determined by sampling the initial voltage before the application of the pulse voltage by a predetermined number of times and an average peak voltage V2 determined by sampling the peak voltage after the application of the pulse voltage by a predetermined number of times, that is, V0=V2−V1.

13. The liquid type identification method for a light oil according to claim 11, characterized in that the identification control unit is constructed so that the type of the light oil is identified using the voltage output difference V0 obtained for the light oil to be identified, based on calibration curve data as a correlation between temperature and voltage output difference, for predetermined reference light oils previously stored in the identification control unit.

14. The liquid type identification method for a light oil according to claim 11, characterized in that a liquid type voltage output Vout for the voltage output difference V0 at a measuring temperature for the light oil to be identified is corrected in a correlation with the output voltage for the voltage output difference at the measuring temperature for a predetermined threshold referenced light oil.

15. The liquid type identification method for a light oil according to claim 11, characterized in that the liquid type identification sensor heater is a laminated liquid type identification sensor heater in which a heater and an identification liquid temperature sensor are laminated through an insulating layer.

16. The liquid type identification method for a light oil according to claim 11, characterized in that the heater and identification liquid temperature sensor in the liquid type identification sensor heater each are constructed so as to come into contact with the light oil to be identified through a metallic fin.

17. The liquid type identification method for a light oil according to claim 11, characterized in that the liquid temperature sensor is constructed so as to come into contact with the light oil to be identified through the metallic fin.

18. The liquid type identification method for an automotive light oil, for identifying the type and distillation properties of the light oil, comprising:
identifying the type and distillation properties of the light oil in a light oil tank or on the upstream side or downstream side of a light oil pump, by using any of the methods for identifying the liquid type of the light oil according to claim 11.

19. An automotive exhaust gas reduction method, comprising the steps of:
identifying the type and distillation properties of the light oil in a light oil tank or on the upstream side or downstream side of a light oil pump, by using the method for identifying the liquid type of a light oil of claim 11, and
regulating an ignition timing based on the type of the light oil which is identified by the liquid type identification apparatus for a light oil.

20. An automotive exhaust gas reduction method, comprising the steps of:
identifying the type and distillation properties of the light oil in a light oil tank or on the upstream side or downstream side of a light oil pump, by using a method for identifying liquid type of a light oil according to claim 11, and
regulating the compression ratio of the light oil based on the type of the light oil which is identified by the liquid type identification apparatus for a light oil.

21. A liquid type identification apparatus for a light oil, for identifying the type and distillation properties of a light oil, comprising:
a liquid type identification chamber for a light oil, for allowing a light oil to be identified, which has been introduced into a liquid type identification apparatus body, to temporarily stay therein; and
a liquid type identification sensor heater provided within the light oil type identification chamber;
the liquid type identification apparatus further comprising an identification control unit;
the identification control unit being constructed such that a pulse voltage is applied to the liquid type identification sensor heater for a predetermined period of time, and the light oil to be identified which temporarily stays within the liquid type identification chamber for a light oil is heated by the liquid type identification sensor heater, and the liquid type of the light oil is identified with a voltage output difference $V0$, corresponding to a temperature difference between the initial temperature and the peak temperature.

* * * * *